United States Patent [19]

MacRitchie

[11] 4,168,000
[45] Sep. 18, 1979

[54] SUTURE PACKAGE

[75] Inventor: David C. MacRitchie, New Milford, Conn.

[73] Assignee: American Cyanamid Company, Stamford, Conn.

[21] Appl. No.: 855,847

[22] Filed: Nov. 30, 1977

Related U.S. Application Data

[63] Continuation-in-part of Ser. No. 734,800, Oct. 22, 1976, abandoned.

[51] Int. Cl.² ............................................. A61L 17/02
[52] U.S. Cl. ................................... 206/63.3; 206/210
[58] Field of Search ...................... 206/210, 63.3, 363

[56] References Cited

U.S. PATENT DOCUMENTS

| 3,202,273 | 8/1965 | Riall | 206/63.3 |
| 3,221,873 | 12/1965 | Bowes et al. | 206/63.3 |
| 3,545,608 | 12/1970 | Berger et al. | 206/63.3 |
| 3,939,969 | 2/1976 | Miller et al. | 206/63.3 |

FOREIGN PATENT DOCUMENTS

| 469054 | 12/1928 | Fed. Rep. of Germany | 206/63.3 |
| 1409244 | 7/1965 | France | 206/63.3 |

Primary Examiner—William Price
Assistant Examiner—Joseph Man-Fu Moy
Attorney, Agent, or Firm—Charles F. Costello, Jr.

[57] ABSTRACT

A catgut suture package is disclosed which upon opening exposes the looped end of a catgut suture. The suture loop is directly dispensed from the package leaving the label intact within the envelope.

11 Claims, 4 Drawing Figures

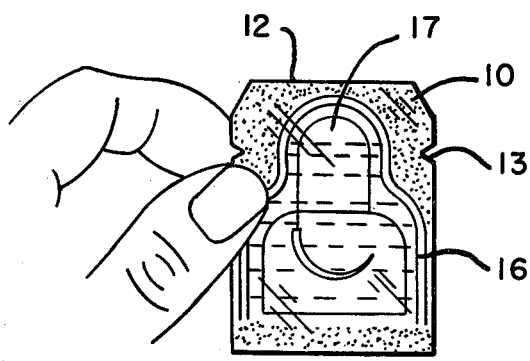
FIG.1
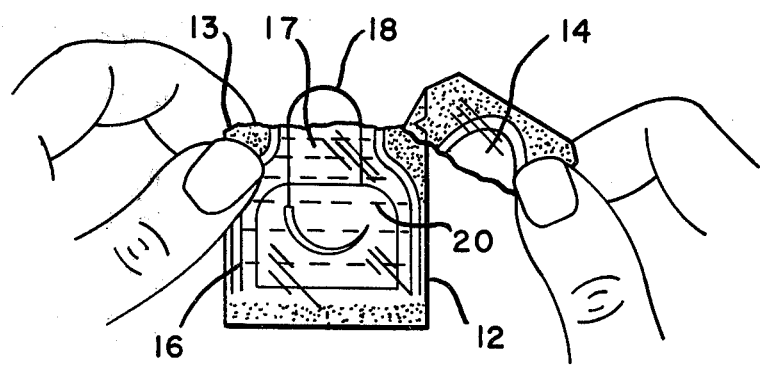
FIG.2
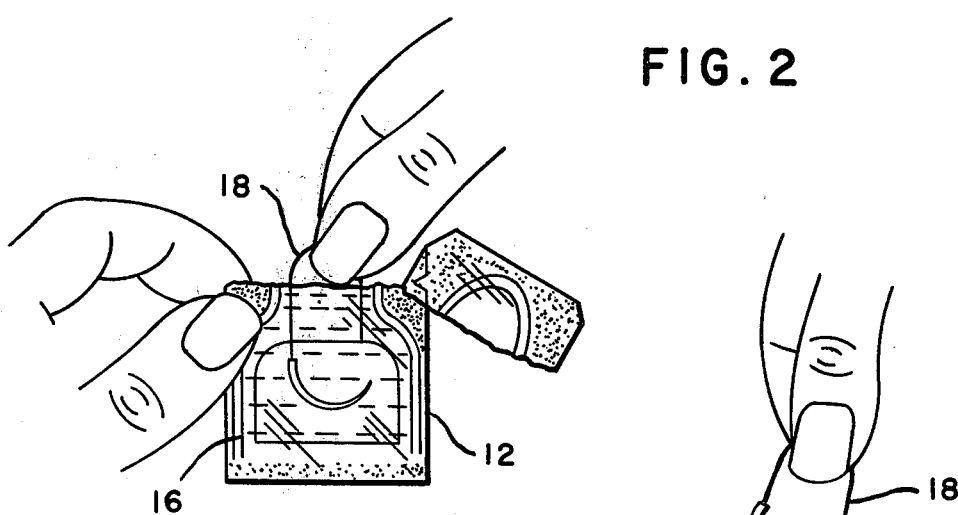
FIG.3
FIG.4

SUTURE PACKAGE

RELATED TO OTHER APPLICATIONS

This application is a continuation-in-part of Ser. No. 734,800, filed Oct. 22, 1976, now abandoned.

BACKGROUND OF THE INVENTION

This invention relates to a suture package which permits direct dispensing of a sterile surgical suture with or without a needle attached. More specifically, to a suture package having a bell shaped configuration that can be torn from a tear notch across the lower portion of the bell shape to expose a looped end of the sterile surgical suture. A suture is a strand of material suitable for suturing, with or without an attached needle, used for ligating or other surgical procedures.

The packaging of many commercial products is essential to the proper and use of the product and thus forms an integral part of the overall product design. The significance of packaging is most evident in the packaging of surgical sutures. It is essential that the package protect the product and maintain sterility throughout its period of potential use. Sutures may be stored in hospitals for several years, although the usual storage time is much shorter. It is essential that the package provide rapid and positive means of identification and release the product undamaged ready for use by the surgeon. There are many sizes of sutures, and many materials of construction such as catgut or polyglycolic acid for absorbables, silk, cotton, nylon, dacron, polyethylene, polypropylene, stainless steel, insulated stainless steel and other materials for use as nonabsorbables. There are several different needle types in common use including pointed straight, pointed curved, three cornered straight, three cornered curved, curved both regular and reverse cutting, and needles with side cutting edges of various types. The variations and combinations of each of these to meet the preference of many surgeons for different operative procedures means that the suture manufacturer needs to supply different suture combinations running into the thousands. The importance of positive identification and efficient, economical packaging can thus be readily appreciated.

It is also important to provide convenience to the use and limit the risk of accidently enclosing foreign items in the patient by limiting the number of extraneous packaging materials associated with use of the product in the operating theater. A count is often kept to ensure that each item is accounted for and removed from the operating field. Considering the ramifications of enclosing such material in the patient accidently during surgical procedures, it is obviously essential to minimize this hazard.

It is also important that the surgical package properly present the suture suitably oriented within the package so that the user can rapidly and reliably have access to the suture end, either needled or non-needled, in the proper position for dispensing from the package.

It is important also, to provide a standard packaging format for all multiple suture materials to limit confusion on the part of the user during surgical procedures. Over the years various package styles have evolved that have detracted from user convenience and operating room efficiency. For purposes of storage in the hospital as well as economy of manufacture, it is highly desirable that as many suture combinations as feasible be packaged in a minimum number of different package styles and shapes and storage units. It is quite common to package 3 dozen identical sutures in a box. It is convenient to have most of the boxes about the same size and shape, so that the hospital may store them most conveniently. It is also convenient from the manufacturers stand point to be able to reduce his inventory of box sizes and to be able to use the same components for the maximum number of suture combinations in the product line.

It is essential that a package containing a needled surgical suture protect the suture from contact with the sharp point or cutting edge of the needle which could partially cut or fray the suture.

These requirements are so rigorous and of such importance that many different package designs have been tried. Applicant is not aware of any prior art reference which, in his respective judgment as one skilled in the suture packaging art, would anticipate or render obvious the suture package of the instant invention; however, for the purpose of fully developing the background of the invention and establishing the state of the requisite art, the following references are set forth: U.S. Pat. Nos. 3,939,969; 3,357,550; 3,221,873; 3,202,273; and 2,949,181. These patents are incorporated herein by reference. Generally, these patents disclose a surgical suture packaged in an outer plastic or foil strippable envelope. Contained in the strippable envelope is an inner or pouch which is sterile. The suture strand has been formed into various retainers, labels, or reels, within the inner envelope.

The suture is normally prepared for the surgeon by stripping the outer envelope and transferring the inner envelope by sterile forceps, or by projecting it across a sterile barrier, into the sterile areas of the operating room. The inner envelope is opened at the time of use.

The inner envelope and suture retaining label of the present invention for a needled or non-needled suture have advantages over these prior art patents. After tearing the inner envelope of the present invention, the suture retaining label is used for direct dispensing of the suture without extracting the label from the inner envelope. Access to the suture is provided by a loop at the suture and which is pulled after tearing the inner envelope. The suture unwinds from its array within the package upon pulling the loop.

Because the inner envelope, the torn portion of the inner envelope, and the suture retaining label remain together after opening, the proliferation of packaging materials within the immediate area of the operation or other surgical procedure is reduced. In most operations and surgical procedures, the materials used for the operation or surgical procedure are counted subsequent to the operation or surgical procedure. The label, the inner envelope and the torn portion of the inner envelope of the present invention provide a readily identifiable and countable package.

Further, the size of the needle and the type of suture strand can be printed on the suture retaining label. This provides ready identification in a surgical procedure where more than one size and type of suture is used. Also, because the inner envelope is clear, the size and type of suture and needle can be confirmed visually before the suture is dispensed.

Perhaps of most importance and the greatest advantage to the package of the invention is the bell shaped configuration of the top portion of the inner envelope.

The bell shaped seal allows more surface area for grasping by the hand. When the inner envelope contains a liquid e.g., a conditioning liquid or softening solution, the bell shaped configuration eliminates or minimizes the squirting of the liquid or solution by hand pressure on the envelope. The bell shaped configuration also gives a "bottle effect" to the package. The wider seal gives more rigidity and support to the top of the package even after opening. This tends to keep the opening closed. Also, because there is a narrower opening, the flow of the liquid is restricted. Also, the narrower opening tends to retain the liquid within the larger end of the package after it is opened.

The Bell shaped configuration is unusual in the heat sealing art generally and in suture packaging specifically. In the heat sealing art, a contoured shape can be more difficult to fabricate because of closer tolerances in the tool design of the sealer, and in sealing pressure applied.

The usual configuration in suture packaging is rectangular with the remaining side being a chevron or "cathedral roof" configuration. See, e.g., U.S. Pat. Nos. 3,357,550; 3,256,981 and 2,949,181 which are incorporated herein by references.

Perhaps of equal importance to the bell shaped configuration is the direct dispensing of the suture strand from the package of this invention.

In the prior art, the suture strand has been contained in or on various retainers, labels, or reels. The suture is dispensed by opening the package, e.g. by tearing or peeling, pulling out the wrapped suture, and then unwinding or separating the suture from its wrapper.

The package of this invention is direct dispensing. Upon opening the package, the suture is directly removed from the package without having to unwind or separate the suture from its retainer label. This has the advantage of saving time, which in a surgical procedure can be of extreme importance. Another advantage of the direct dispensing package of this invention is that the suture is directly dispensed from the end. The suture is thus readily available for immediate use, either by hand or by use of a needle holder. Still another advantage is that the suture retainer label is retained in the package after direct dispensing of the suture. This has the advantage of reducing the amount of loose packaging materials in the surgical area. Still another advantage is that, because an accounting is usually made after a surgical procedure, the inner envelope, the torn portion of the inner envelope, and the retainer label can be counted as one piece after direct dispensing of the surgical suture.

Still another advantage of the package of this invention is the textured surface of the sealed area. This allows for a secure grip, for example, by the thumb and index finger. Also, because of the textured surface, the amount of hand pressure which would have to be applied to the sealed area during tearing may be reduced.

SUMMARY OF THE INVENTION

A direct dispensing suture package has been invented. By direct dispensing is meant that only the suture is removed from the sealed envelope, after the envelope is opened.

This direct dispensing suture package comprises a transparent envelope which is heat sealed. On three sides of the envelope, the heat seal is adjacent the edge. On the remaining side, the heat seal is a bell shaped configuration. In the preferred embodiment, the package perimeter is rectangular.

Adjacent the lower portion of the bell shaped configuration, and on the edge of the package is at least one notch. The lower portion of the bell shaped configuration is the widest part of the bell shape. In the preferred embodiment, two notches are adjacent the lower portion on opposite edges of the package.

A textured surface for gripping by hand is adjacent the bell shaped configuration. The textured surface allows for a secure grip by the thumb and index finger of the user. The textured surface is of such a size as to prevent hand pressure on the bell shaped configuration by the user.

A label is contained in the envelope and is larger than the bell shaped configuration. Thus when the suture is directly dispensed from the envelope, the label is retained in the package. In the preferred embodiment, the label is folded into about four equal parts. The geometry of the folds is not critical as long as a suture strand is held in the label and the suture is directly dispensed after the package is opened. In another embodiment, the label is folded into at least about two equal parts horizontally from the bottom. In yet another embodiment, the label is folded into at least about two equal parts vertically from one side.

In another preferred embodiment, the label contains identifying information on the suture and/or the needle. Because the envelope is transparent, the identifying information can be contained on both sides of the label.

A suture strand is held in the label described above. In the preferred embodiment, the end of the suture strand looped into the bell shaped configuration is needled.

In another preferred embodiment, the envelope contains a conditioning liquid. In the most preferred embodiment, the envelope contains a conditioning liquid wherein the suture strand is catgut and the end of the suture strand is needled.

In other embodiments, the suture strand held in the label described above is either nylon, dacron, polyethylene or polypropylene.

The configuration of the suture strand in the label is not critical to the practice of this invention except that the configuration must allow for direct dispensing of the suture when the envelope is opened. In this regard, a figure eight and a serpentine configuration have been found to be effective. These configurations are therefore preferred.

The end of the suture strand is looped into the bell shaped configuration.

The end of the suture strand is available for visual identification without opening the package. The end of the suture strand, because it is looped into the bell shaped configuration, prevents the suture strand in the label from being damaged. This is especially important when the end of the suture strand is needled. The bell shaped configuration is opened from the notch to the opposite lower portion of the bell shape. The end of the suture strand is then pulled by hand or by a needle holder for direct dispensing from the package. The suture strand unwinds within the envelope. The label is left with the package and the bell shape configuration is left on the envelope.

BRIEF DESCRIPTION OF THE DRAWINGS

FIG. 1 is a front view of the envelope describing the bell shaped seal, the notched edges and the textured surface at the smaller end of the envelope.

FIG. 2 is a front view of the envelope illustrating the opening of the envelope by hand-tearing across the smaller end. The wide heat seal area tends to prevent hand pressure on the fluid and to eliminate squirting.

FIG. 3 is a front view of the opened envelope illustrating the ease of grasping the loop of catgut suture situated in the smaller end of the enclosure. The torn portion is not detached from the envelope.

FIG. 4 is a front view of the inner envelope illustrating the direct dispensing of catgut suture from the envelope. The label remains within the envelope.

DESCRIPTION OF THE PREFERRED EMBODIMENT

This invention relates to catgut sutures which are needled and non-needled. The envelope contains a conditioning liquid which is required for the preservation of catgut sutures. Conventional conditioning liquids include ethyl alcohol or a mixture of ethyl alcohol, isopropyl alcohol, and water. Conditioning liquids can also contain a germicidal agent, and/or a rust inhibitor to prevent rusting of needles which may be attached to the sutures.

Although the bell shaped configuration of the package of this invention is particularly suited to envelopes containing a suture in a conditioning liquid, it is to be understood that other suture materials such as nylon, dacron, polyethylene and polypropylene could be directly dispensed from the package without the conditioning liquid. The invention is more fully described in the figures.

Referring to FIG. 1, on envelope 12 has been contoured heat sealed 16 to form an enclosure 17 which is smaller at one end. The contoured bell shaped configuration provides an enclosure for a dispensing loop of the invention. The outer edge of the envelope 12 is notched 13 near the lower portion of the bell shape. The contoured heat sealed area around the bell shape is textured 10.

As shown in FIG. 3, the envelope 12 is opened by hand-tearing, beginning at the notch 13, across the smaller enclosure. This exposes an extended loop 18 of the enclosed catgut suture. The amount of conditioning liquid 20 in the envelope is such that when the envelope is opened, the level of the liquid is below the torn portion 14 of the envelope. The torn portion 14 is not detached from the envelope 12.

FIGS. 3 and 4 illustrate the direct dispensing of the catgut suture. In FIG. 3, the catgut suture and 18 is grasped for removal from the envelope. In FIG. 4 the suture is removed by direct dispensing of the catgut suture and 18, either by hand as described or by needle holder. The catgut suture is directly dispensed by unwinding within the package. The label 19 and the conditioning liquid 20 are retained within the larger end of the envelope.

The envelope can be designed from two separate, flexible, transparent sheets. While other flexible transparent materials, such as polyamid (or nylon), may be used, it is preferred that the envelope consist of a laminate having an external surface of a polyester film, such as the polyester of theylene glycol and terephthalic acid, which is sold under the trademark "Mylar" with an interior polyethylene or The envelope can be formed by adhesively uniting the films. It is preferred, however, to heat seal the films on the inside.

The suture is folded in the label and inserted into the envelope. In the preferred embodiment, the suture is folded in a figure eight or serpentine configuration in the label. The label can be made of any foldable sheet material, such as paper.

The label retains the suture is a configuration for direct dispensing within the larger end of the inner envelope. The label also provides identifying information, e.g. as to the length, size, and type of the suture and the needle.

The envelope can be sterilized by either radiation or by placing the envelope in a sterilizing chamber containing sterilizing gas, such as ethylene oxide.

The description of this invention is for preferred embodiments only. Any modifications which are within the scope of the claims and which suggest themselves to those skilled in the art are within the scope of this invention.

I claim:

1. A direct dispensing suture package comprising:
   a transparent envelope being heat sealed to form an enclosure, said enclosure comprising a label chamber and a bell-shaped chamber, each chamber including two side portions and one end portion, said side portions of said label chamber being substantially parallel and then converging toward each other to meet the side wall portions of said bell-shaped chamber, the width of said label chamber being greater than said bell-shaped chamber;
   at least one tearing notch adjacent one of said side portions of said bell-shaped chamber, said tearing notch being located to permit tearing action across said bell-shaped chamber;
   a textured surface for gripping by hand adjacent said side porions of said bell-shaped chamber, said surface of such a size as to prevent hand pressure on said bell-shaped chamber;
   a label folded into at least about two equal parts contained in said label chamber, the width of said folded label being larger than said bell-shaped chamber;
   a needled suture strand held in said label, with the end of said strand looped into said bell-shaped chamber, and with the needle laid onto said label for preventing said suture strand from being damaged by said needle, whereby when said bell-shaped chamber is opened from said notch and the end of said strand is pulled by hand or by a needle holder, said strand is directly dispensed from said package by unwinding within said envelope, leaving said label in said label chamber.

2. The package described in claim 1 wherein said label is folded into about four equal parts.

3. The package described in claim 1 wherein said label is folded horizontally from the bottom.

4. The package described in claim 1 wherein said label is folded vertically from one side.

5. The package described in claim 1 wherein said label contains suture identifying information.

6. The package described in claim 1 wherein said envelope contains a conditioning liquid.

7. The package described in claim 6 wherein said strand is catgut.

8. The package described in claim 1 wherein said strand is nylon.

9. The package described in claim 1 wherein said strand is dacron.

10. The package described in claim 1 wherein said strand is polyethylene.

11. The package described in claim 1 wherein said strand is polypropylene.

* * * * *